(12) United States Patent
Andersen et al.

(10) Patent No.: US 11,013,839 B2
(45) Date of Patent: *May 25, 2021

(54) SUCTION DEVICE

(71) Applicant: MÖLNLYCKE HEALTH CARE AB, Gothenburg (SE)

(72) Inventors: Bjarne Andersen, Fredrikssund (DK); Malin Bringsved, Gothenburg (SE); Sofia Frantzich, Mölnlycke (SE); Ulf Johannison, Landvetter (SE); Johan Uveborn, Askim (SE); Karsten Videbaek, Jyllinge (DK)

(73) Assignee: MÖLNLYCKE HEALTH CARE AB, Gothenburg (SE)

(*) Notice: Subject to any disclaimer, the term of this patent is extended or adjusted under 35 U.S.C. 154(b) by 434 days.

This patent is subject to a terminal disclaimer.

(21) Appl. No.: 16/000,944

(22) Filed: Jun. 6, 2018

(65) Prior Publication Data

US 2018/0280596 A1  Oct. 4, 2018

Related U.S. Application Data

(63) Continuation of application No. 14/761,335, filed as application No. PCT/EP2014/051562 on Jan. 28, 2014, now Pat. No. 10,016,546.

(Continued)

(30) Foreign Application Priority Data

Jan. 28, 2013  (EP) .................................... 13152841

(51) Int. Cl.
*A61M 35/00* (2006.01)
*A61M 1/00* (2006.01)
(Continued)

(52) U.S. Cl.
CPC ..... *A61M 1/0088* (2013.01); *A61F 13/00068* (2013.01); *A61M 1/0023* (2013.01);
(Continued)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS

| | | |
|---|---|---|
| 4,778,446 A | 10/1988 | Jensen |
| 5,116,310 A | 5/1992 | Seder et al. |

(Continued)

FOREIGN PATENT DOCUMENTS

| | | |
|---|---|---|
| EP | 0620720 A1 | 10/1994 |
| EP | 0777504 A1 | 6/1997 |

(Continued)

OTHER PUBLICATIONS

U.S. Appl. No. 61/109,360, filed Oct. 29, 2008, Hirsch.
(Continued)

*Primary Examiner* — Tatyana Zalukaeva
*Assistant Examiner* — Ilya Y Treyger
(74) *Attorney, Agent, or Firm* — Ballard Spahr LLP

(57) ABSTRACT

The present invention relates to a suction device. The suction device comprises an attachment portion adapted to be attached to a wound cover member. The suction device comprises a fluid inlet which is at least partially circumscribed by the attachment portion. The suction device also comprises a fluid outlet. The suction device further comprising a connection portion adapted to, at least during one operation condition of the suction device, provide a fluid communication between the fluid inlet and the fluid outlet. The connection portion comprises an inspection portion that
(Continued)

is transparent to thereby facilitate the positioning of the suction device relative to the wound cover member.

12 Claims, 5 Drawing Sheets

Related U.S. Application Data

(60) Provisional application No. 61/757,242, filed on Jan. 28, 2013.

(51) Int. Cl.
| | |
|---|---|
| *A61F 13/00* | (2006.01) |
| *B29C 45/26* | (2006.01) |
| *B29C 45/76* | (2006.01) |
| *A61M 27/00* | (2006.01) |
| *A61F 13/02* | (2006.01) |
| *B29K 75/00* | (2006.01) |
| *B29L 31/00* | (2006.01) |

(52) U.S. Cl.
CPC .......... *B29C 45/2602* (2013.01); *B29C 45/76* (2013.01); *A61M 2205/583* (2013.01); *A61M 2207/00* (2013.01); *A61M 2210/04* (2013.01); *B29K 2075/00* (2013.01); *B29K 2995/0026* (2013.01); *B29L 2031/7546* (2013.01)

(56) References Cited

U.S. PATENT DOCUMENTS

| | | | |
|---|---|---|---|
| 5,636,643 | A | 6/1997 | Argenta et al. |
| 5,645,081 | A | 7/1997 | Argenta et al. |
| 6,142,982 | A | 11/2000 | Hunt et al. |
| 6,345,623 | B1 | 2/2002 | Heaton et al. |
| 6,553,998 | B2 | 4/2003 | Heaton et al. |
| 6,814,079 | B2 | 11/2004 | Heaton et al. |
| 7,004,915 | B2 | 2/2006 | Boynton et al. |
| 7,195,624 | B2 | 3/2007 | Lockwood |
| 7,198,046 | B1 | 4/2007 | Argenta et al. |
| 7,216,651 | B2 | 5/2007 | Argenta et al. |
| 7,553,306 | B1 | 6/2009 | Hunt et al. |
| 7,758,555 | B2 | 7/2010 | Kelch et al. |
| 8,216,197 | B2 | 7/2012 | Simmons et al. |
| 8,287,506 | B2 | 10/2012 | Wells et al. |
| 8,460,258 | B2 | 6/2013 | Jones et al. |
| 8,771,244 | B2 | 7/2014 | Eckstein et al. |
| 8,784,392 | B2 | 7/2014 | Vess et al. |
| 8,801,685 | B2 | 8/2014 | Armstrong et al. |
| 8,900,217 | B2 | 12/2014 | Malhi |
| D738,487 | S | 9/2015 | Andersen et al. |
| 9,327,065 | B2 | 5/2016 | Albert et al. |
| D786,421 | S | 5/2017 | Andersen et al. |
| D788,292 | S | 5/2017 | Andersen et al. |
| 9,642,750 | B2 | 5/2017 | Albert et al. |
| 2004/0002670 | A1 | 1/2004 | Mothersbaugh et al. |
| 2006/0173253 | A1 | 8/2006 | Ganapathy et al. |
| 2006/0173523 | A1 | 8/2006 | Rainey et al. |
| 2007/0129660 | A1 | 6/2007 | McLeod et al. |
| 2008/0195017 | A1 | 8/2008 | Robinson et al. |
| 2008/0208171 | A1 | 8/2008 | Argenta et al. |
| 2008/0275409 | A1 | 11/2008 | Kane et al. |
| 2009/0227968 | A1 | 9/2009 | Vess |
| 2009/0281526 | A1 | 11/2009 | Kenny et al. |
| 2010/0010477 | A1 | 1/2010 | Augustine et al. |
| 2010/0106108 | A1 | 4/2010 | Hirsch |
| 2010/0137775 | A1 | 6/2010 | Hu et al. |
| 2010/0160901 | A1 | 6/2010 | Hu et al. |
| 2010/0185163 | A1 | 7/2010 | Heagle |
| 2010/0318071 | A1 | 12/2010 | Wudyka |
| 2011/0015619 | A1 | 1/2011 | Svedman et al. |
| 2011/0106058 | A1 | 5/2011 | Svedman et al. |
| 2011/0184361 | A1 | 7/2011 | Crojzat et al. |
| 2011/0196278 | A1 | 8/2011 | Svedman et al. |
| 2012/0010578 | A1 | 1/2012 | Hirsch |
| 2015/0359951 | A1 | 12/2015 | Andersen et al. |
| 2017/0196736 | A1 | 7/2017 | Long et al. |
| 2017/0290709 | A1 | 10/2017 | Adie et al. |

FOREIGN PATENT DOCUMENTS

| | | |
|---|---|---|
| EP | 0853950 A1 | 7/1998 |
| EP | 0865304 A1 | 9/1998 |
| EP | 1018967 A1 | 7/2000 |
| EP | 1088569 A2 | 4/2001 |
| EP | 1219311 A2 | 7/2002 |
| EP | 1440667 A1 | 7/2004 |
| GB | 1549756 A | 8/1979 |
| JP | 2011-523870 A | 8/2011 |
| WO | WO-1993/009727 A1 | 5/1993 |
| WO | WO-1996/005873 A1 | 2/1996 |
| WO | WO-1997/018007 A1 | 5/1997 |
| WO | WO-1999/013793 A1 | 3/1999 |
| WO | WO-2009/016195 A2 | 2/2009 |
| WO | WO-2009/146441 A1 | 12/2009 |
| WO | WO-2010/105179 A3 | 9/2010 |
| WO | WO-2011/087871 A2 | 7/2011 |

OTHER PUBLICATIONS

U.S. Appl. No. 61/289,358, filed Dec. 22, 2009, Albert et al.
U.S. Appl. No. 61/332,440, filed May 7, 2010, Albert et al.
U.S. Appl. No. 61/369,008, filed Jul. 29, 2010, Albert et al.
International Search Report and Written Opinion mailed by the International Searching Authority dated May 6, 2014 for International Application No. PCT/EP2014/051562, which was published as WO 2014/114804 on Jul. 31, 2014 (Inventors—Bringsved, et al.; Applicant—Molnlycke Health Care AB) (14 pages).
European Search Report and Written Opinion dated Jan. 7, 2014 by the European Patent Office for European Patent Application No. 13152841.6, which was filed on Jan. 28, 2013 and published as 2759310 on Jul. 30, 2014 (Inventor—Andersen et al.; Applicant—Molnlycke Health Care AB) (6 pages).
Intention to Grant dated Oct. 8, 2015 by the European Patent Office for European Patent Application No. 13152841.6, which was filed on Jan. 28, 2013 and published as 2759310 on Jul. 30, 2014 (Inventor—Andersen et al.; Applicant—Molnlycke Health Care AB) (42 pages).
*Medela AG v. Molnlycke Health Care AB*, Landgericht München I (Munich District Court I) Kammer für Patentstreitsachen (Court for Patent Cases), filed Nov. 30, 2015 (Original—14 pages // Translated—15 pages).
KCI Operating Procedures, The V.A.C. (Vacuum Assisted Closure)—V.A.C.® TherapyTM Clinical Guidelines. KCI Licensing, Inc. (2005) (37 pages).
Medela AG, Negative Pressure Wound Therapy: True NPWT®—Simplicity Without Compromise. Distributed by Joerns®. Medela AG. (2014) (6 pages).
Smith&Nephew, Renasys—Negative Pressure Wound Therapy: Supplies & Accessories. Smith&Nephew, Inc. (2011) (5 pages).
Exhibit 1010, Expert Declaration by Dr. Michael Helmus, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (185 pages).
Exhibit 1011, Expert Declaration by Carianne Nilsson, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (14 pages).
Exhibit 1019, KCI User's Manual, Dec. 2006, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (77 pages).
Exhibit 1020, Trademark Prosecution History for SENSAT.R.A.C., of the Petition for Post-Grant review filed by Molnlycke Health

(56) References Cited

OTHER PUBLICATIONS

Care AB for U.S. Pat. No. 9,642,750, which was filed before the Patent Trial and Appeal Board on Feb. 9, 2018; Case No. PGR2018-00035 (113 pages).
Exhibit 1021, Presentation from KCI, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (31 pages).
Exhibit 1022, Certified English Translation of "Presentation from KCI," of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (31 pages).
Exhibit 1023, Certification of Translation of "Presentation from KCI," of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (2 pages).
Exhibit 1024, KCI Launches Next Generation Wound Care Therapy Systems, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (3 pages).
Exhibit 1025, KCI Product Catalog, 2009, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (5 pages).
Exhibit 1026, KCI User's Manual, Mar. 5, 2010, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (3 pages).
Exhibit 1027, 510K filing K062227 by KCI with the Food and Drug Administration on Sep. 27, 2006, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (6 pages).
Exhibit 1028, 510K filing K022011 by KCI with the Food and Drug Administration on Jun. 19, 2002, of the Petition for Post-Grant review filed by Molnlycke Health Care AB for U.S. Pat. No. 9,642,750, which was filed before the Patent Trial and Appeal Board on Feb. 9, 2018; Case No. PGR2018-00035 (6 pages).
Exhibit 1029, Images of SensaTRAC Produced in 2016, of the Petition for Post-Grant review filed by Molnlycke Health Care AB for U.S. Pat. No. 9,642,750, which was fi ed before the Patent Trial and Appeal Board on Feb. 9, 2018; Case No. PGR2018-00035 (6 pages).
Atkins, B.Z. et al., Does Negative Pressure Wound Therapy Have a Role in Preventing Poststernotomy Wound Complications? Surgical Innov. 2009; 16(2):140-6.
Banasiewicz, T. et al., Vacuum-assisted Closure Therapy in Patients with large Postoperative Wounds Complicated by Multiple Fistulas. Widochir Inne Tech Maloinwazyjne. 2011; 6(3):155-63.
Graham, J.S. et al., Medical Management of Custaneous Sulfur Mustard Injuries. Toxoicology (2008) doi: 10.1016/j.tox.2008.07.067 (12 pages).
Lavery, L.A., DPM and Murdoch, D.P., DPM, Emerging Concepts with VAC Therapy. Podiatry Today. 2007 (20(7):84-91.
Von Rüden, C. et al., Bogota—VAC—A Newly Modified Temporary Abdominal Closure Technique. Eur J Trauma Emerg Surgery. 2008; 34(6):582-6.
SensaT.R.A.C.™ Technology: An Essential Component of V.A.C.® Therapy. KCI Healing by Design. 2010 (2 pages).
The Clincally Proven Benefits of the Integrated V.A.C.® Therapy System. KCI Healing by Design. 2009 (10 pages).
Trademark Electronic Search System. TRAC Pad. Serial No. 76450743, which was filed on Sep. 18, 2002. KCI Licensing, Inc. (2 pages).
V.A.C. Freedom® and V.A.C. ATS® Therapy Systems: Active Healing by Design. v.a.c.® therapy: KCI Healing by Deisgn. 2009 (4 pages).
V.A.C.® ATS User Manual, KCI: The Clinical Advantage. Revised Aug. 12, 2003 (14 pages).
Vacuum-Assisted Closure for the Management of Wounds: An Accelerated Systematic Review. ASERNIP-S Report No. 37. Australian Safety and Efficacy Register of New Interventional Procedures-Surgical. The Royal Australasian College of Surgeons. Dec. 2003 (53 pages).
Examination Report No. 1 dated Apr. 28, 2017 by the Australian Patent Office for Patent Application No. 2014209801, which was filed on Jun. 10, 2015 and published on Jul. 2, 2015 (Inventor—Andersen et al.; Applicant—Mölnlycke Health Care AB) (3 pages).
Notice of Acceptance dated Jul. 6, 2017 by the Australian Patent Office for Patent Application No. 2014209801, which was filed on Jun. 10, 2015 and published on Jul. 2, 2015 (Inventor—Andersen et al.; Applicant—Mölnlycke Health Care AB) (3 pages).
Decision to Grant dated Sep. 28, 2017 by the European Patent Office for Patent Application No. 13152841, which was filed on Jan. 28, 2013 and published as EP 2759310 on Jul. 30, 2014 (Inventor—Andersen et al.; Applicant—Mölnlycke Health Care AB) (2 pages).
Decision of Rejection dated Aug. 1, 2017 by the Patent Office of Japan for Patent Application No. 2015-554188, which was filed on Jan. 28, 2014 and published as Jp 2016- 504137 on Feb. 12, 2016 (Inventor—Andersen et al.; Mölnlycke Health Care AB) (Translation only—6 pages).
International Search Report and Written Opinion dated Sep. 8, 2011 by the International Searching Authority for International Application No. PCT/US2010/061938, which was filed on Dec. 22, 2010 and published as WO 2011/087871 on Jul. 21, 2011 (Applicant—Smith & Nephew, Inc.; Inventor—Albert, et al) (18 pages).
International Preliminary Report on Patentability dated Jun. 26, 2012 by the International Searching Authority for International Application No. PCT/US2010/061938, which was filed on Dec. 22, 2010 and published as WO 2011/087871 on Jul. 21, 2011 (Applicant—Smith & Nephew, Inc.; Inventor—Albert, et al) (11 pages).
International Preliminary Report on Patentability dated Jul. 28, 2015 by the International Searching Authority for Patent Application No. PCT/EP2014/051562, which was filed on Jan. 1, 2014 and published as WO 2014/114804 on Jul. 31, 2014 (Inventor—Andersen et al.; Applicant—Mölnlycke Health Care AB) (8 pages).
Preliminary Amendment filed on Feb. 16, 2016 by the U.S. Patent and Trademark Office for U.S. Appl. No. 15/018,724, filed Feb. 8, 2016, now U.S. Pat. No. 9,642,750 on May 9, 2017 (Inventor—Albert et al.; Applicant—Smith & Nephew, Inc.) (6 pages).
Notice of Allowance dated Mar. 9, 2017 by the U.S. Patent and Trademark Office for U.S. Appl. No. 15/018,724, filed Feb. 8, 2016, now U.S. Pat. No. 9,642,750 on May 9, 2017 (Inventor—Albert et al.; Applicant—Smith & Nephew, Inc.) (8 pages).
Post Allowance Communication filed on Apr. 4, 2017 with the U.S. Patent and Trademark Office for U.S. Appl. No. 15/018,724, filed Feb. 8, 2016 now U.S. Pat. No. 9,642,750 on May 9, 2017 (Inventor—Albert et al.; Applicant—Smith & Nephew, Inc.) (2 pages).
Issue Notification dated Apr. 19, 2017 by the U.S. Patent and Trademark Office for Patent Application No. 15/018,724, filed Feb. 8, 2016, now U.S. Pat. No. 9,642,750 on May 9, 2017 (Inventor—Albert et al.; Applicant—Smith & Nephew, Inc.) (1 page).
Post-Grant Review Petition filed by Mölnlycke Health Care AB before the Patent Trial and Appeal Board on Feb. 9, 2018 for U.S. Pat. No. 9,642,750; Case No. PGR2018-00035 (86 pages).
Notice of Opposition dated Feb. 21, 2020 by the European Patent office for EP Application No. 14701545.7, which was filed on Jan. 28, 2014 and published as EP 2948199 on Dec. 2, 2015 (Applicant—Mölnlycke Health Care AB) (162 pages).
Leach, R., Optical Measurement of Surface Topography. Springer Berlin Heidelberg. Mar. 31, 2011; ISBN 978-3-642-12011-4; eBook ISBN978-6-642-12012-1, Extract, E2 (26 pages).
Notice of Opposition dated Jul. 24, 2018 by the European Patent Office for Patent Application No. 1315284.6, which was filed on Jan. 28, 2013 and published as EP 2759310 on Jul. 30, 2014 (Inventor—Andersen et al.; Applicant—Mölnlycke Health Care AB) (16 pages).

SUCTION DEVICE

CROSS-REFERENCE TO RELATED APPLICATIONS

This application is a continuation application of U.S. application Ser. No. 14/761,335, filed Jul. 16, 2015, which is a U.S. National Phase Application of International Application No. PCT/EP2014/051562, filed Jan. 28, 2014, which claims priority to European Patent Application No. 13152841.6, filed Jan. 28, 2013, and U.S. Provisional Application No. 61/757,242, filed Jan. 28, 2013, each of which are hereby incorporated by reference in their entirety.

TECHNICAL FIELD

The present disclosure relates to a suction device. Moreover, the present disclosure relates to a method for producing a suction device.

BACKGROUND

Some types of wounds are advantageously treated by so called negative pressure wound therapy. In the field of negative pressure wound therapy, a negative pressure is applied to the wound for a relatively long time and it has been realized that the healing process may be expedited by using such a wound therapy.

To this end, a negative pressure wound therapy system may be used which generally comprises a wound cover member that is adapted to be placed over a wound. The system further generally comprises a negative pressure source, such as a vacuum pump, which is in fluid communication with the wound cover member via a fluid communication assembly that comprises a suction device.

For instance, WO99/13793 discloses a suction head and surgical drape combination that may be used for applying suction to a wound area. In the combination disclosed in WO99/13793, the suction head is adapted to be placed inside a portion of the surgical drape.

Alternatively, the suction device may be adapted to be attached to the outside of the wound cover member, for instance by means of an adhesive layer located on the suction device, such that a fluid inlet of the suction device is in fluid communication with an opening in the wound cover member.

In order to obtain an appropriate fluid communication between the suction device's fluid inlet and the wound cover member opening, it is generally desired that the fluid inlet of the suction device be placed over the wound cover member opening. The operation of correctly attaching the suction device to the wound cover member may be cumbersome.

SUMMARY

One object of the present disclosure is to provide a suction device for a negative pressure wound therapy system, which suction device facilitates the placement thereof relative to a wound cover member opening of the negative pressure wound therapy system.

This object is achieved by a suction device according to claim 1.

As such, the present disclosure relates to a suction device. The suction device comprises an attachment portion adapted to be attached to a wound cover member. The suction device comprises a fluid inlet being at least partially circumscribed by the attachment portion. The suction device also comprises a fluid outlet and the suction device further comprises a connection portion adapted to, at least during one operation condition of the suction device, provide a fluid communication between the fluid inlet and the fluid outlet.

Purely by way of example, the suction device may be suitable for a negative pressure wound therapy system. Moreover, although purely by way of example, the wound cover member may form a part of the negative pressure wound therapy system.

The connection portion comprises an inspection portion that is transparent to thereby facilitate the positioning of the suction device relative to the wound cover member.

The fact that the inspection portion is transparent implies that an operator, striving to attach the suction device to the wound cover member, will experience a possibility to see the wound cover member opening, or at least a marker of the wound cover member indicative of the position of the wound cover member opening, through the inspection portion.

Such a possibility in turn implies that the operator may be able to place the suction device at a position on the wound cover member in which the fluid inlet of the suction device is located above the wound cover member opening.

Moreover, by virtue of the fact that the inspection portion is transparent, it may be possible to monitor exudates that are transferred from the wound cover member towards the negative pressure source via the suction device.

Optionally, the inspection portion has a haze measure that is equal to or less than 50%.

The definition of the haze measure, as well as a test method for obtaining a measured value thereof, is presented in Example 1 hereinbelow. A haze measure equal to or below the above limit implies that an appropriate transparency may be obtained for the inspection portion.

Alternatively, the haze measure may be equal to or less than any one of the following upper limits: 45%, 40%, 35%, 30%, 25% and 20%. As another option, the haze measure may be equal to or less than 32%.

Optionally, the inspection portion has a total light transmittance of at least 50%. As another option, the inspection portion has a total light transmittance of at least 60%. Optionally, the inspection portion has a total light transmittance of at least 70%.

The definition of total light transmittance, as well as a test method for obtaining a measured value thereof, is presented in Example 1 hereinbelow.

The provision of a total light transmittance equal to or more than at least one of the above limits implies that it may be possible to see the wound cover member opening, or at least a marker of the wound cover member indicative of the position of the wound cover member opening, through the inspection portion even if the process of attaching the suction device to the wound cover member is performed in a condition with relatively low illumination.

Optionally, the inspection portion may have a surface roughness, when using a surface roughness measure that is the average angle of surface slopes $S_{dq}$, that is less than or equal to $S_{dq}$ 20°. The feature that the surface roughness is less than or equal to $S_{dq}$ 20° implies that an appropriate transparency may be obtained for the inspection portion. Alternatively, the inspection portion may have a surface roughness that is less than or equal to $S_{dq}$ 17°.

Optionally, the inspection portion may have a surface roughness, when using a measure that is the percentage of increased area compared to a plane $S_{dr}$, that is less than or equal to $S_{dr}$ 5%. The feature that the surface roughness that is less than or equal to $S_{dr}$ 5% implies that an appropriate transparency may be obtained for the inspection portion. Alternatively, the inspection portion may have a surface roughness that is less than or equal to $S_{dr}$ 3.5%.

Optionally, the inspection portion may have a surface roughness, when using a measure that is the average deviation from average surface plane $S_a$, that is less than or equal to $S_a$ 1500 nm. Alternatively, the surface roughness of the inspection portion may be equal to or less than any one of the following upper limits: 1400 nm, 1300 nm and 1200 nm.

Optionally, the inspection portion is delimited by an inner surface and an outer surface, the inner surface being located closer to the fluid inlet than the outer surface. Optionally, at least the outer surface of the inspection portion has a surface roughness measure within any one of the above discussed limits. As another option, each one of the inner surface and the outer surface has a surface roughness measure within any one of the above discussed limits.

Optionally, the inspection portion has a thickness within the range of 0.2 to 1.5 mm, alternatively within the range of 0.4 to 1.0 mm. As another example, the inspection portion has a thickness within the range of 0.7 to 0.9 mm. The inspection portion thickness within any one of the above discussed ranges may have the advantage of enabling appropriate see-through characteristics of the inspection portion and also providing an inspection portion that has an appropriately low risk of collapsing when a negative pressure is applied to the negative pressure wound therapy system.

Optionally, the inspection portion is made of polyurethane.

Optionally, the inspection portion has a total surface area of at least 10 mm². As other examples, the inspection portion has a total surface area of at least 15 mm², at least 25 mm², at least 50 mm² or at least 70 mm². A surface area of the inspection portion equal to or above any one of the above limits implies an appropriately large field of view for the operator.

Optionally, the inspection portion may have a total surface area that is equal to or less than 100 mm², alternatively less than or equal to 80 mm². A surface area of the inspection portion equal to or below any one of the above limits implies that an operator will be able to view only a relatively limited area of the wound cover member through the inspection portion and this in turn implies that the operator may be able to determine, with a relatively high degree of certainty, whether or not the inspection portion aligns with the wound cover member opening.

Optionally, the inspection portion is a continuous portion. The feature that the inspection portion is a continuous portion implies that the operator will have a sufficiently un-obscured view through the inspection portion towards the wound cover membrane. As another option, the inspection portion may be discontinuous, i.e. comprising two or more sub-portions. The one or more sub-portions may for example be separated from one another by portions with a relatively low transparency of the connection portion. As a non-limiting example, an inspection portion may comprise two sub-portions each one of which having a surface area of at least 20 mm². As another non-limiting example, the two sub-portions may have different surface areas and a first sub-portion may have a surface area of at least 30 mm² and a second sub-portion may have a surface area of at least 40 mm².

Optionally, the inspection portion is configured so as to have a magnifying effect such that at least a portion of the fluid inlet, when looked upon through the inspection portion, is magnified by the inspection portion. Such a magnifying effect of the inspection portion may facilitate the placing of the suction device in an appropriate position on the wound cover member.

Optionally, the inspection portion is delimited by an inner surface and an outer surface, the inner surface being located closer to the fluid inlet than the outer surface. At least the outer surface has convex shape.

Optionally, the connection portion comprises a duct wall at least partially defining a connection duct from the inlet to the outlet. The duct wall comprises the inspection portion, the connection portion comprising a partition wall extending at least partially from the duct wall.

By virtue of the presence of the partition wall, the risk of having the connection portion collapse, e.g. during an installation procedure and/or during a negative pressure therapy, is reduced. As such, the presence of the partition wall implies that the connection portion may substantially maintain its intended shape during at least an installation procedure.

This in turn implies that an appropriate field of view will be obtained through the inspection portion. Moreover, the presence of the partition wall implies that the wall thickness of the inspection portion can be reduced, while still obtaining appropriate structural characteristics of the connection portion. The above discussed thickness reduction generally implies improved see-through characteristics of the inspection portion.

Optionally, the fluid outlet extends in a longitudinal direction and the partition wall extends in a partition wall extension that is substantially parallel to the longitudinal direction. The above orientation of the partition wall in relation to the extension of the fluid outlet implies that a reinforcement of the connection portion is obtained, which reinforcement will have a limited negative influence on the flow between the suction device's inlet and its fluid outlet.

As used herein, the expression "substantially parallel" means that a first vector, extending in the longitudinal direction, and a second vector, extending in the partition wall extension, intersect one another at an angle that is equal to or less than 30°.

Optionally, the inlet extends in a circumferential direction, the inlet further extending in an axial direction being substantially perpendicular to the circumferential direction, wherein a projection of at least a portion of the partition wall, in the axial direction and towards the inlet, is located within the inlet. By virtue of the fact that at least a portion of the partition wall is located within the inlet, the risk of having the connection portion collapse may be further reduced. Moreover, the feature that a portion of the partition wall is located within the inlet implies a reduced risk of having e.g. wound cover member flaps transported through the suction device.

A second aspect of the present disclosure relates to a kit for a negative pressure wound therapy system. The kit comprises:
 a suction device according to the first aspect of the present disclosure, and
 a wound cover member adapted to be attached over a wound.

Optionally, the wound cover member comprises a wound cover film.

Optionally, the kit further comprises fluid communication means adapted to provide a fluid communication between the fluid outlet and a negative pressure source.

A third aspect of the present disclosure relates to a method for producing a suction device. The suction device comprises an attachment portion adapted to be attached to a wound cover member. The suction device comprises a fluid inlet being at least partially circumscribed by the attachment portion. The suction device also comprises a fluid outlet and the suction device further comprises a connection portion adapted to, at least during one operation condition of the suction device, provide a fluid communication between the fluid inlet and the fluid outlet. The connection portion comprises an inspection portion.

The method comprises:
  providing a mould for the suction device, the mould comprising a mould inspection portion corresponding to the inspection portion of the connection portion, the mould inspection portion having a surface roughness, when using a surface roughness measure that is the average angle of surface slopes $S_{dq}$, less than or equal to $S_{dq}$ 15°, and
  injecting a curable material into the mould.

Purely by way of example, the suction device produced in accordance with the above discussed method may be suitable for a negative pressure wound therapy system. Moreover, although purely by way of example, the wound cover member may form a part of the negative pressure wound therapy system.

Optionally, the mould inspection portion may have a surface roughness, when using a measure that is the percentage of increased area compared to a plane $S_{dr}$, that is less than or equal to $S_{dr}$ 4%. As another alternative, the surface roughness of the mould inspection portion may be less than or equal to $S_{dr}$ 3.5%.

Optionally, the curable material comprises polyurethane.

A fourth aspect of the present disclosure relates to a method comprising:
providing a cover member,
providing a suction device comprising
i. an attachment portion for attachment to the cover member,
ii. a fluid inlet at least partially circumscribed by the attachment portion,
iii. a fluid outlet,
iv. a connection portion that allows fluid communication between the fluid inlet and fluid outlet, wherein the connection portion comprises an inspection portion that is transparent,
providing the cover member with an opening,
positioning the suction device such that the fluid inlet aligns with the opening in the cover member.

Optionally, the above method further comprises applying suction to the suction device.

BRIEF DESCRIPTION OF THE DRAWINGS

With reference to the appended drawings, below follows a more detailed description of embodiments of the invention cited as examples.

In the drawings.

It should be noted that the appended drawings are not necessarily drawn to scale and that the dimensions of some features of the present invention may have been exaggerated for the sake of clarity.

Definitions

Haze measure: As used herein, the phrase "haze measure" (also known as "haze value" or "transmission haze") refers to its ordinary meaning in the art, and describes the amount of light that is scattered as it passes through a material. As used herein, the "haze measure" is calculated as the ratio of diffuse light transmittance over total light transmittance. (See Equation 2 in Example 1 hereinbelow)

Surface roughness: As used herein, the term "surface roughness" refers to its ordinary meaning in the art, and provides a measure of the texture of a surface based on vertical deviations of a surface from its ideal form.

In particular the area surface roughness parameters $S_a$ (average deviation from average surface plane), $S_{dq}$ (average angle of surface slopes) as well as $S_{dr}$ (percentage of increased area compared to a plane) may be determined in accordance with the following standards: ISO 25178-2:2009 and ISO 25178-3:2009. See also Example 3 hereinbelow.

Inspection portion: As used herein, the phrase "inspection portion" (also referred to as "inspection window") refers to a portion that is characterized by optical properties that allow, for example, a user or an optical device, using light in the visible light spectrum, to see through to the other side of the inspection portion. The inspection portion may be one continuous portion. Alternatively, the inspection portion may be comprised of more than one part. In embodiments in which the inspection portion is comprised of more than one part, the more than one part(s) may be equal or unequal in surface area to each other.

DETAILED DESCRIPTION OF PREFERRED EMBODIMENTS

The invention will, in the following, be exemplified by embodiments. It is to be understood, however, that the embodiments are included in order to explain principles of the invention and not to limit the scope of the invention defined by the appended claims.

Figure 1:
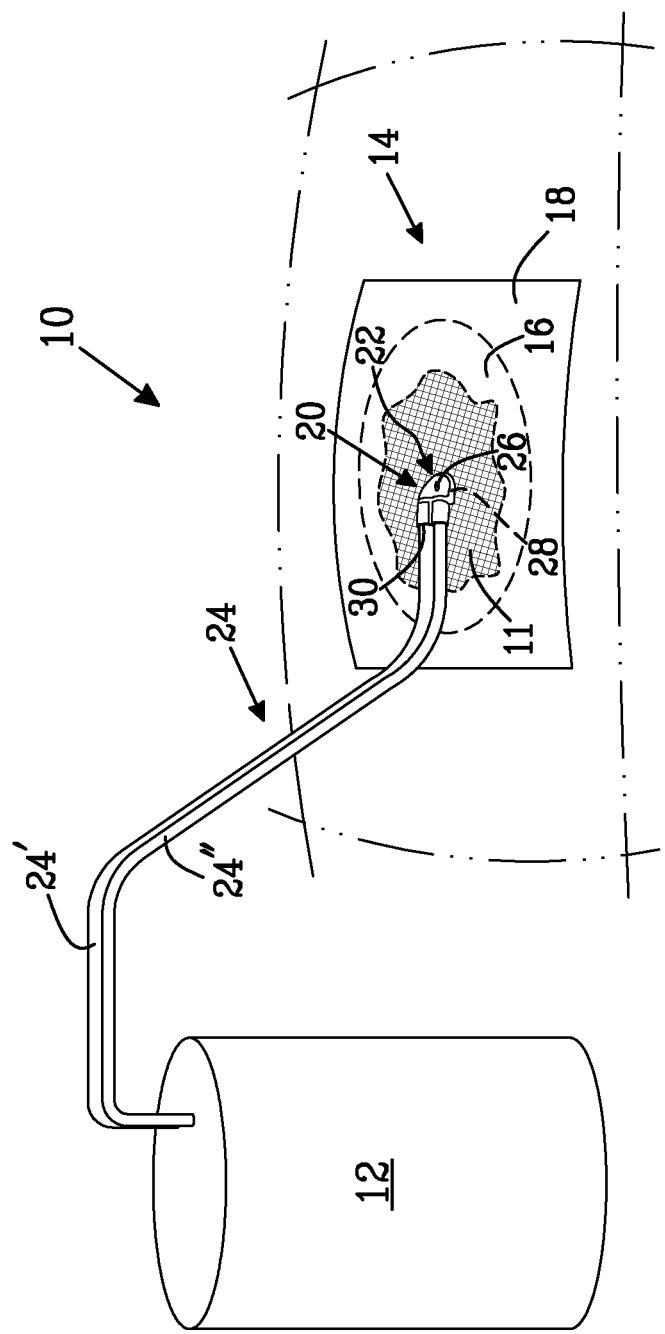
FIG. 1 illustrates an embodiment of a negative pressure wound therapy system.

FIG. 1 illustrates a negative pressure wound therapy system 10. The purpose of the negative pressure wound therapy system 10 is to obtain a negative pressure in the area of a wound 11.

The negative pressure system illustrated in FIG. 1 comprises a negative pressure source 12, which in FIG. 1 is implemented as a vacuum pump. Moreover, FIG. 1 illustrates that the system 10 comprises a wound cover assembly 14.

The implementation of the wound cover assembly 14 illustrated in FIG. 1 comprises a wound filler 16 which is adapted to be placed on or in the wound to be treated by the negative pressure wound therapy. Purely by way of example, the wound filler 16 may comprise an absorbent material, such as open-celled foam material. As a non-limiting example, the wound filler 16 may comprise a flexible open-celled foam material, such as a sponge material. Moreover, the FIG. 1 implementation of the wound cover assembly 14 comprises a wound cover member 18 adapted to cover the wound filler 16.

The wound cover member 18 is generally adapted to be attached to the skin surrounding the wound. Purely by way of example, the wound cover member 18 may comprise a wound cover film. The wound cover member 18 may preferably be attached to the skin by an adhesive. Examples of adhesives that may be used include, but are not limited to, acrylic adhesives and/or silicone gel adhesives. In some embodiments, the adhesive or adhesives is/are already incorporated as part of the wound cover film. In some embodiments, the adhesive or adhesives is/are applied to the wound cover member during use. Purely by way of example, the adhesive sold under the trademark Mepiseal® by Mölnlycke Healthcare AB may be used for attaching the wound cover member to the skin surrounding the wound.

FIG. 1 further illustrates that the negative pressure wound therapy system 10 comprises a fluid communication assembly 20 adapted to provide a fluid communication between the negative pressure source 12 and the wound cover member 18.

Figure 6:
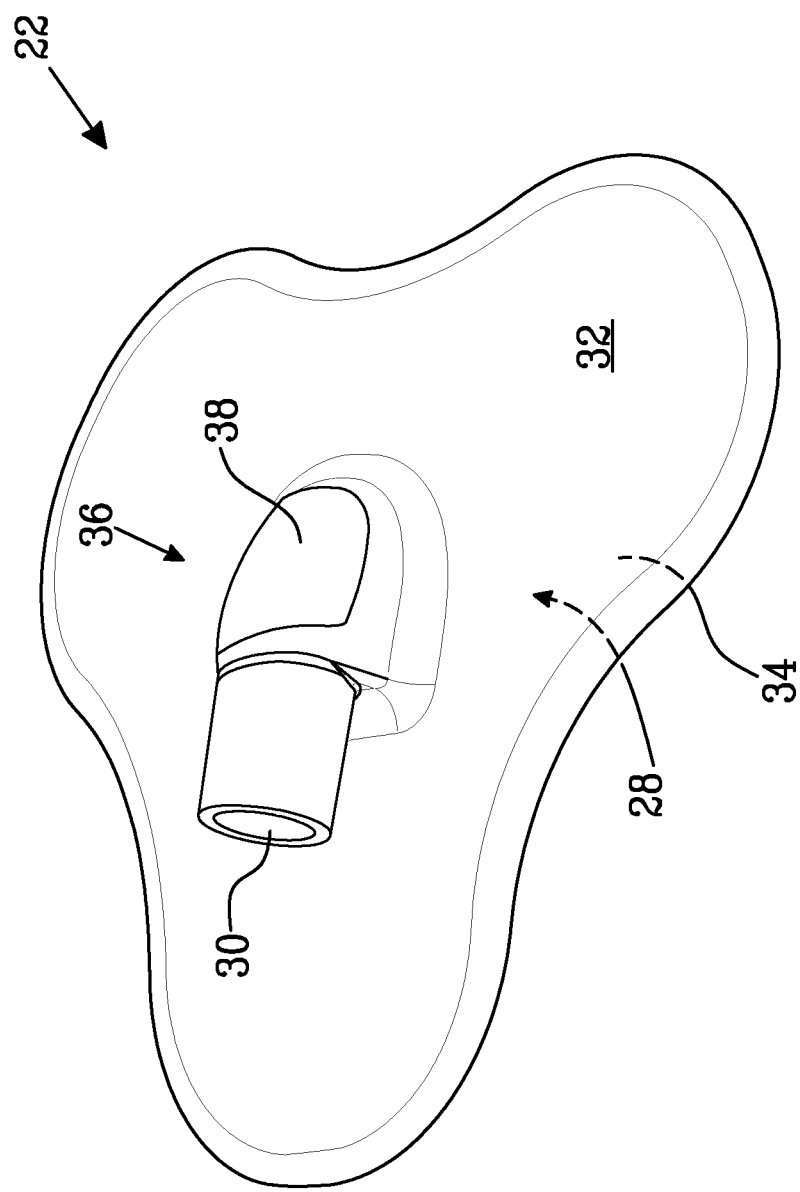
FIG. 6 illustrates a perspective view of another embodiment of a suction device.

The fluid communication assembly 20 may preferably comprise a suction device 22 and a conduit assembly 24 comprising one or more conduits. The implementation of the fluid communication assembly 20 illustrated in FIG. 1 comprises two conduits, viz a first conduit 24' and a second conduit 24". Embodiments in which only one conduit is provided are also contemplated, see e.g. the embodiment of the suction device 22 illustrated in FIG. 6. The conduit assembly 24 is adapted to provide a fluid communication between the wound therapy system 10 and the suction device 22.

The FIG. 1 negative pressure wound therapy system 10 is adapted to apply a negative pressure to the volume at least partially enclosed by the wound cover member 18 through the first conduit 24'. In embodiments in which a second conduit is provided, the second conduit 24" may be used for introducing an air volume (e.g., ambient air, re-circulated air from the system) at a pressure level that is larger than the pressure level provided by the negative pressure source 12 into the volume least partially enclosed by the wound cover member 18.

A purpose of introducing the air volume can be, for example, to monitor and/or dissolve a blockage or obstruction that could possibly occur in the first conduit 24'. Purely by way of example, the negative pressure wound therapy system 10 may preferably comprise a dosing feeder (not shown) adapted to feed a volume of air into the volume at least partially enclosed by the wound cover member 18 upon request by an operator and/or on a regular basis. As a non-limiting example, the pressure of the air volume introduce via the second conduit 24" may be an atmospheric pressure. Purely by way of example, the dosing feeder may comprise a valve (not shown) located in or on the negative pressure source 12.

The wound cover member 18 comprises a wound cover member opening 26 allowing a fluid passage through the wound cover member 18. Purely by way of example, the wound cover member opening 26 may be pre-cut in the wound cover member 18. As another non-limiting example, the wound cover member opening 26 may be obtained after the wound cover member 18 has been arranged over the wound filler 16. For instance, the wound cover member opening 26 may be cut by a cutting tool such as a knife or a scalpel.

The suction device 22 comprises a fluid inlet 28 and a fluid outlet 30. In order to obtain the desired negative pressure in the area of a wound 11, it is generally desired that the fluid inlet 28 covers the wound cover member opening 26.

Figure 2:
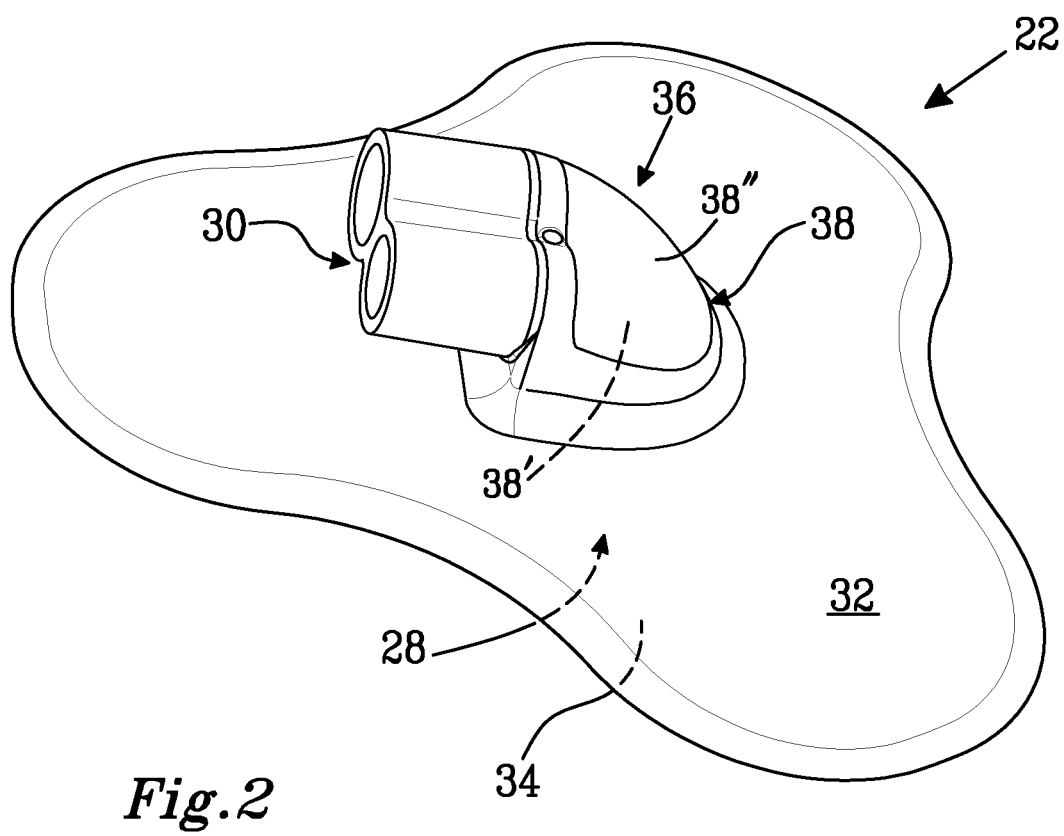
FIG. 2 illustrates a perspective view of an embodiment of a suction device.

FIG. 2 illustrates an embodiment of the suction device 22 according to the present invention. The suction device comprises an attachment portion 32 adapted to be attached to the wound cover member 18 of the negative pressure wound therapy system 10. Purely by way of example, the attachment portion 32 may comprise an adhesive layer 34 adapted to be attached to the wound cover member (not shown in FIG. 2).

Moreover, the FIG. 2 suction device 22 comprises a fluid inlet 28 being at least partially circumscribed by the attachment portion 32. In the FIG. 2 embodiment of the suction device 22, the fluid inlet 28 is completely circumscribed by the attachment portion 32.

FIG. 2 further illustrates that the suction device 22 also comprises a fluid outlet 30. The fluid outlet 30 is adapted to be in fluid communication with the negative pressure source 12. Purely by way of example, the fluid outlet 30 may be fluid communication with the negative pressure source 12 via the above discussed conduit assembly 24.

As may be gleaned from FIG. 2, the suction device 22 further comprises a connection portion 36 adapted to, at least during one operation condition of the suction device 22, provide a fluid communication between the fluid inlet 28 and the fluid outlet 30. In the FIG. 2 embodiment of the suction device 22, the connection portion 36 is adapted to provide a permanent fluid communication between the fluid inlet 28 and the fluid outlet 30.

FIG. 2 further illustrates that the connection portion 36 comprises an inspection portion 38. The inspection portion 38 is transparent to thereby enable that at least a portion of the fluid inlet 28 can be viewed through the inspection portion 38. Thus, the inspection portion 38 is relatively clear such that it, from the outside of the inspection portion 38, is possible to identify the position of the wound cover member opening (not shown in FIG. 2).

To this end, although purely by way of example, the inspection portion may have a haze measure that is equal to or less than 50%.

Alternatively, the haze measure may be equal to or less than any one of the following upper limits: 45%, 40%, 35%, 30% and 25%. As another option, the haze measure may be equal to or less than 32%.

Moreover, the inspection portion 38 may preferably have a total light transmittance of at least 50%, alternatively at least 60%. As another option, the total light transmittance may be at least 70%.

The definition of the haze measure and the total light transmittance, as well as a test method for obtaining a measured value thereof, is presented in Example 1 hereinbelow.

The above discussed properties of the inspection portion 38, i.e. the haze measure and possibly also the total light transmittance, may be obtained in a plurality of ways. Purely by way of example, the material of the inspection portion 38 may be different from the material of the attachment portion 32.

As a non-limiting example, at least the inspection portion 38 may be made of polyurethane. Moreover, the inspection portion 38 may have a thickness that is within the range of 0.2 to 1.5 mm, alternatively within the range of 0.4 to 1.0 mm. As another non-limiting example, the thickness of the inspection portion 38 may be within the range of 0.7 to 0.9 mm.

Furthermore, although purely by way of example, the inspection portion 38 may have a surface roughness, when using a measure that is the average angle of surface slopes $S_{dq}$, that is less than or equal to $S_{dq}$ 20°. Alternatively, the inspection portion 38 may have a surface roughness that is less than or equal to $S_{dq}$ 17°.

Optionally, although purely by way of example, the inspection portion 38 may have a surface roughness, when using a surface roughness measure that is the percentage of increased area compared to a plane $S_{dr}$, that is less than or equal to $S_{dr}$ 5%. Alternatively, the inspection portion 38 may have a surface roughness that is less than or equal to $S_{dr}$ 3.5%.

As another non-limiting option, an implementation of the inspection portion 38 may have a surface roughness that is less than or equal to $S_{dq}$ 20° as well as less than or equal to $S_{dr}$ 5%.

Moreover, it is envisaged that an implementation of the inspection portion 38 has a surface roughness, when measured as the average deviation from average surface plane $S_a$, that is less than or equal to 1500 nm. It is further envisaged that implementations of the inspection portion have a surface roughness measure $S_a$ that is less than or equal to 1500 nm in addition to a surface roughness measure of $S_{dq}$ less than or equal to 20° and/or a surface roughness measure of $S_{dr}$ less than or equal to 5%.

Examples of surface roughness data for an embodiment of a suction device 22 is presented in Example 3 hereinbelow.

In the FIG. 2 implementation, the inspection portion 38 is delimited by an inner surface 38' and an outer surface 38". The inner surface 38' is located closer to the fluid inlet 28 than the outer surface 38".

According to an implementation of the inspection portion 38, at least the outer surface 38" has a surface roughness measure within any one of the above discussed surface measure roughness limits, viz the measure that is the average angle of surface slopes $S_{dq}$ and/or the measure that is the percentage of increased area compared to a plane $S_{dr}$ and/or the measure that is the average deviation from average surface plane $S_a$.

Moreover, the inner surface 38' may be sufficiently smooth such that the inspection portion 38 provides appropriate transparency characteristics.

According to a non-limiting implementation of the inspection portion 38, the inner surface 38' may have a surface roughness measure that corresponds to the surface measure limits of the outer surface 38".

As another option, each one of the inner surface 38' and the outer surface 38" has a surface roughness measure within any one of the above discussed limits.

As another non-limiting example, at least the attachment portion 32 and the connection portion 36, including the inspection portion 38, of the suction device 22 may form a unitary component. For instance, both the attachment portion 32 and the connection portion 36 may be made of polyurethane. Optionally, the entire suction device 22 is made of polyurethane. Instead of, or in addition to polyurethane, at least a portion of the suction device 22 may be made of at least one of the following materials: other types of urethanes, silicone, transparent hydrocolloid, PVC, hydrogel, copolyester, polyethylene, TPS (thermoplastic elastomers based on styrene) or TPO (thermoplastic olefins) i.e. blends of polyethylenes and polypropylenes.

Purely by way of example, the suction device 22 may be flexible. This may be achieved by for instance making at least portions of the suction device 22 of one or more flexible materials, such as polyurethane, silicone, transparent hydrocolloid, soft PVC, hydrogel, copolyester, polyethylene.

Although characteristics indicative of the transparency have been discussed hereinabove with reference to the inspection portion 38, it is also envisaged that embodiments of the suction device 22 may comprise one or more additional portions that is/are transparent. Purely by way of example, such portions may have one or more of the transparency indicative characteristics, such as at least one of the following: the haze measure, the total light transmittance, the material, the thickness and the surface roughness, that have been discussed hereinabove.

As a non-limiting example, an embodiment of the suction device is envisaged wherein substantially the entire suction device is transparent (not shown).

In a similar vein as has been discussed hereinabove, the inspection portion 38 of a suction device 22 in which the attachment portion 32 and the connection portion 36 form a unitary component may have a thickness that is within the range of 1.5 to 0.2 mm, alternatively within the range of 1.0 to 0.4 mm. As another alternative, the thickness may be within the range of 0.7 to 0.9 mm.

Irrespective of whether the inspection portion 38 is of a different material than the material of the attachment portion 32 or if the inspection portion 38 and the attachment portion 32 both are portions of a unitary component, the inspection portion 38 may have a surface area of at least 10 mm². As other examples, the inspection portion 38 has a total surface area of at least 15 mm², at least 25 mm², at least 50 mm² or at least 70 mm².

Moreover, although purely by way of example, the inspection portion may have a total surface area that is equal to or less than or equal to 100 mm², alternatively less than or equal to 80 mm².

As a non-limiting example, the portion of the suction device 22 that encloses the inspection portion 38 may be less transparent than the inspection portion 38. Purely by way of example, in an embodiment of the suction device 22, the haze measure of the portion of the suction device 22 that encloses the inspection portion 38 may be higher than the haze measure of the inspection portion 38.

Moreover, the inspection portion 38 may be a continuous portion. As another alternative, the inspection portion 38 may be discontinuous, i.e. comprising two or more sub-portions. The one or more sub-portions may for example be separated from one another by one or more portions with a relatively low transparency of the connection portion 36.

Purely by way of example, the inspection portion 38 may configured so as to have a magnifying effect such that at least a portion of the fluid inlet 28, when looked upon through the inspection portion 38, is magnified by the inspection portion 38.

An implementation of such an inspection portion is illustrated in FIG. 2 wherein at least the outer surface 38" has a convex shape.

Figure 3:
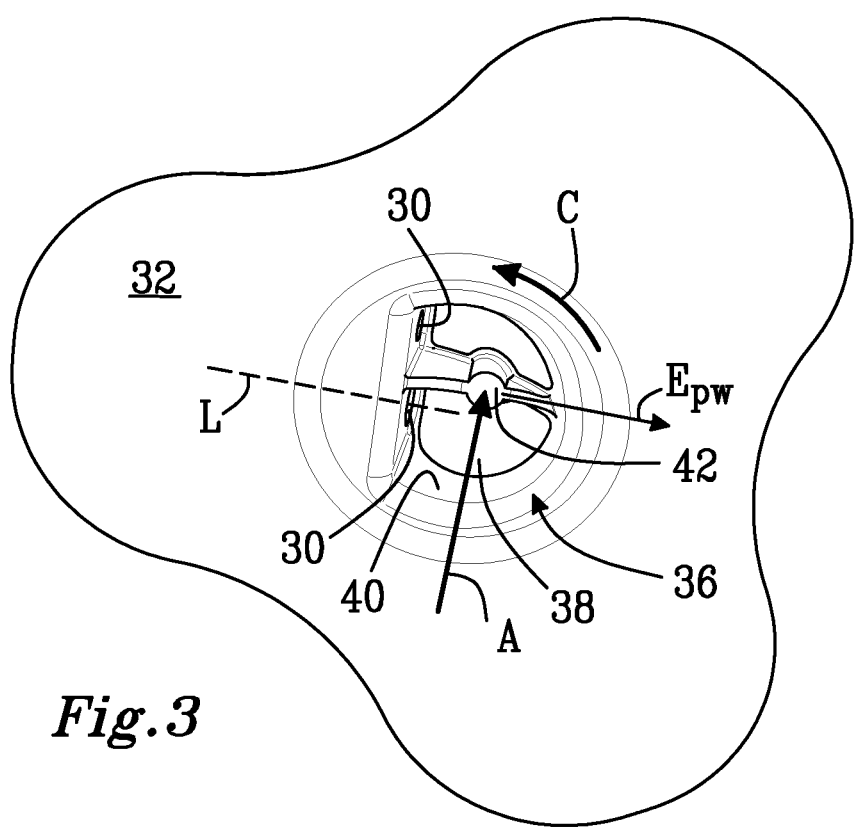
FIG. 3 illustrates a bottom view of the FIG. 2 embodiment.

FIG. 3 is a bottom view of the FIG. 2 embodiment of the suction device 22. FIG. 3 illustrates that the connection portion 36 may comprise a duct wall 40 at least partially defining a connection duct from the fluid inlet 28 to the fluid outlet 30. The duct wall 40 comprises the inspection portion 38. Moreover, the connection portion 36 comprises a partition wall 42 extending at least partially from the duct wall 40. Purely by way of example, the partition wall 42 may be of a different material than the duct wall 40. In an embodiment of the suction device 22, the partition wall 42 and the duct wall 40 form a unitary component.

Moreover, FIG. 3 illustrates an embodiment of the suction device wherein the fluid outlet 30 extends in a longitudinal direction L and the partition wall 42 extends in a partition wall extension $E_{PW}$ that is substantially parallel to the longitudinal direction L.

As a non-limiting example, in an embodiment of the suction device 22, the thickness of the partition wall 42 may be within the range of 0.4 to 1.0 mm. As another example, the thickness may be within the range of 0.5 to 0.8 mm.

FIG. 3 further illustrates that the inlet may extend in a circumferential direction C. Moreover, the fluid inlet also extends in an axial direction A which is substantially perpendicular to the circumferential direction C. Purely by way of example, a projection of at least a portion of the partition wall 42, in the axial direction A and towards the fluid inlet 28, is located within the fluid inlet 28. The above discussed position of at least a portion of the partition wall 42 may reduce the risk of introducing flaps from the wound cover member (not shown in FIG. 3) into the fluid outlet 30.

The structural strength of an embodiment of a suction device 22 comprising a partition wall 42 has been tested by applying a negative pressure to the suction device. The result of the test is presented in Example 4 hereinbelow.

The suction device 22 may be manufactured by injection moulding wherein a curable material is injected into a mould. Purely by way of example, the curable material may comprise polyurethane. As a non-limiting example, at least 80% of the curable material consists of polyurethane.

Once the curable material has cured and the cast moulding has been removed from the mould, at least the inspection portion 38 may be post-treated such that the desired see-through characteristic of the inspection portion is obtained. Purely by way of example, the inspection portion 38 may be polished such that the surface roughness within any one of the above discussed limits may be obtained on the outer surfaces delimiting the inspection portion 38.

Figure 4:
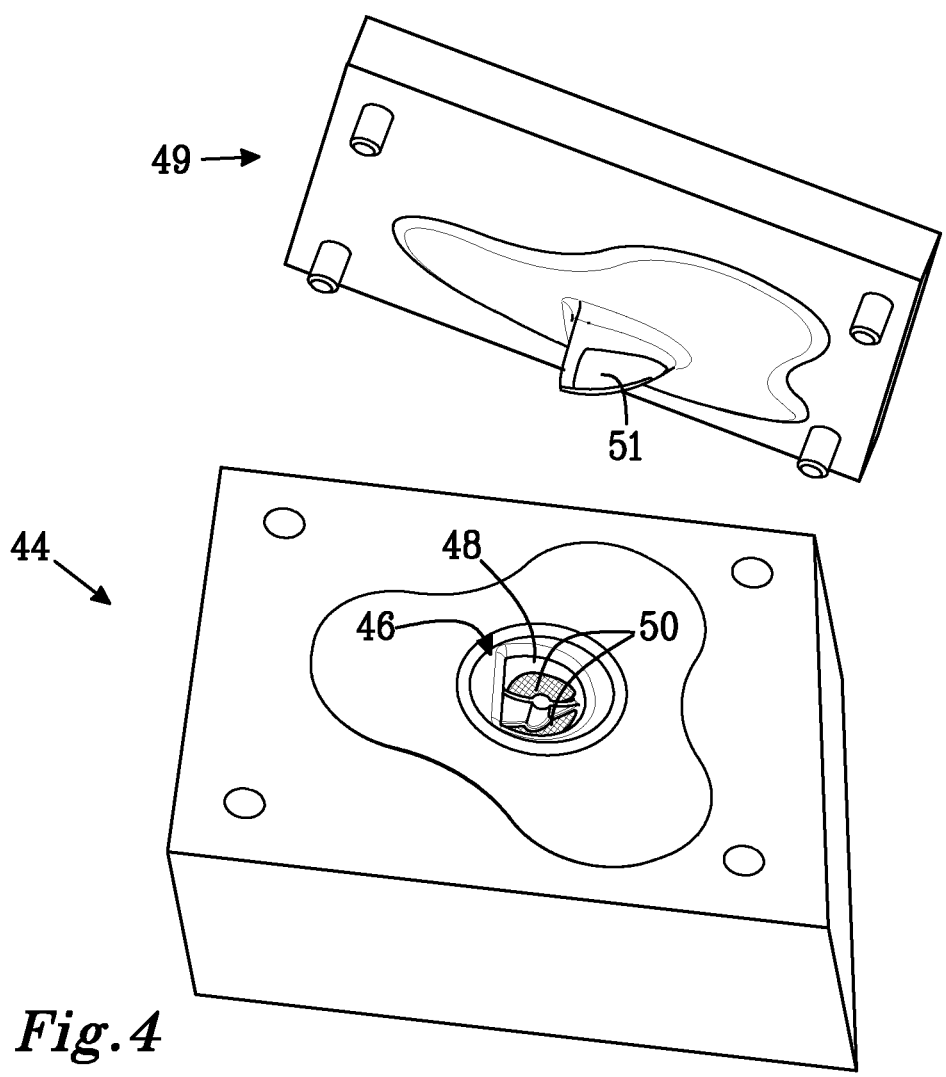
FIG. 4 illustrates a mould suitable for moulding a suction device.

FIG. 4 illustrates a mould 44 that may be used in an embodiment of a method for producing a suction device for a negative pressure wound therapy system. As may be gleaned from FIG. 4, the mould 44 comprises a mould cavity 46, the walls 48 of which mirror the shape of the suction device to be manufactured. The mould 44 further comprises a mould core 49 adapted to be introduced into the mould cavity 46.

Moreover, FIG. 4 illustrates that the mould cavity wall 48 comprises a mould inspection portion 50 that corresponds to the inspection portion 38 of the suction device 22. Purely by way of example, the mould inspection portion 50 has a surface roughness that is lower than a surface roughness of the portion of the cavity wall which encloses the mould inspection portion 50. As a non-limiting example, the surface roughness of the mould inspection portion 50 may be less than or equal to half the surface roughness of the portion of the cavity wall which encloses the mould inspection portion 50.

Purely by way of example, the mould inspection portion 50 has a surface roughness, when using a surface roughness measure that is the average angle of surface slopes $S_{dq}$, of less than or equal to $S_{dq}$ 15°. Instead of, or in addition to above discussed surface roughness measure, the mould inspection portion 50 could have a surface roughness, when using a surface roughness measure that is the percentage of increased area compared to a plane $S_{dr}$, of less than or equal to $S_{dr}$ 4%. As another alternative, the surface roughness of the mould inspection portion 50 may be less than or equal to $S_{dr}$ 3.5%.

Moreover, it is envisaged that an implementation of mould inspection portion 50 may have a surface roughness, when measured as the average deviation from average surface plane $S_a$, that is less than or equal to 1500 nm. Purely by way of example, an implementation of the mould inspection portion 50 may have a surface roughness measure of $S_a$ less than or equal to 1500 nm in addition to a surface roughness measure less than or equal to $S_{dq}$ 15° and/or a surface roughness measure less than or equal to $S_{dr}$ 4%.

As a non-limiting example, an appropriate surface roughness of the mould inspection portion 50 may be achieved by polishing the mould inspection portion 50 using a diamond paste with particles the size of which are 1 micron or less.

As such, by using a mould 44 such as the one illustrated in FIG. 4, an appropriately low surface roughness, and consequently appropriate see-through characteristic, may be obtained for the inspection portion 38 of the suction device 22 thus produced. The above discussed see-through characteristic may for instance be obtained without the need of any post-treatment of the inspection portion 38.

Moreover, for at least some implementations of the mould 44 that has relatively smooth mould inspection portion 50 as has been discussed hereinabove, at least 50% of the mould cavity wall that is located outside of the mould inspection portion may for instance have a surface roughness greater than $S_a$ 1500 nm. The relatively large surface roughness of a relatively large portion of the mould cavity wall implies that the cast mould, once cured, can be released from the mould 44 in a straightforward way.

The mould core 49 may also have a surface roughness, at least in a mould core inspection portion 51 that corresponds to the inspection portion 38 of the suction device 22, of less than or equal to $S_{dq}$ 15°. Instead of, or in addition to the above discussed surface roughness measure, the mould core inspection portion 51 could have a surface roughness of less than or equal to $S_{dr}$ 4%. As another alternative, the surface roughness of the mould core inspection portion 51 may be less than or equal to $S_{dr}$ 3.5%.

As another non-limiting example, a relatively large portion, e.g. more than 50%, of the area of the portion of the mould core 49 that is located outside the mould core inspection portion 51 may have a surface roughness of more than $S_{dq}$ 15°, alternatively of more than $S_{dr}$ 4%.

Finally, it should be recognized that structures and/or elements and/or method steps shown and/or described in connection with any disclosed form or embodiment of the invention may be incorporated in any other disclosed or described or suggested form or embodiment as a general matter of design choice.

EXAMPLE 1

In order to determine the haze measure of inspection portion of a suction device, the test method proposed hereinbelow may be used.

Figure 5:
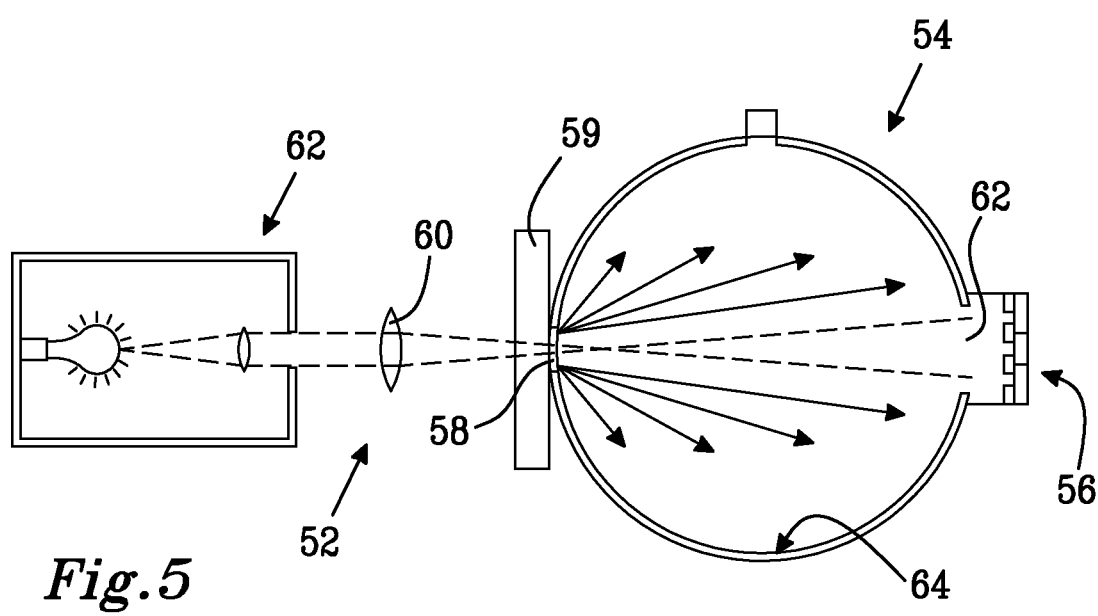
FIG. 5 illustrates a test method for determining the haze measure of an object.

The below test method generally follows the test procedure as presented in ASTM D1003, procedure B. The test procedure is illustrated in FIG. 5. The instrument used for the test method is preferably a Perkin Elmer Lambda 9 UV-Vis-NIR spectrophotometer 52 equipped with an integrating sphere 54. The diameter of the sphere is 6 cm.

A photomultiplier detector 56 is located inside the sphere and protected from direct light by a baffle. The geometry used is unidirectional illumination with diffuse viewing.

A suction device should be tested in the condition that it is intended to assume when the suction device is to be attached to a wound cover member. As such, if the suction device is to be sterilized in a certain manner prior to being attached to the wound cover member, the suction device should consequently be sterilized in the same manner prior to being subjected to the haze measure and/or total light transmittance measurements that are presented hereinbelow.

Typical methods used to sterilize a suction device may comprise ethylene oxide gas sterilization, gas plasma technology, steam sterilization, gamma irradiation, and electron beam irradiation. If there is no specific sterilization method associated with a suction device, the sterilization method as outlined in Example 2 hereinbelow could be employed.

A deviation from the ASTM D1003, procedure B, standard is occasioned by the fact that the size of the inspection portion of a suction device may be smaller than the size of the entrance port 58 of the sphere. As such, a lens 60 is placed between the light source 62 (including the monochromator) and the sphere 54. FIG. 5 further illustrates a sample 59 positioned adjacent to the entrance port 58.

The lens is a convex lens with a focal distance of 8 cm. The distance between the lens and the sample is 4 cm and the distance between the lens and the light source is approximately 1 m.

The lens 60 limits the illuminated area at the entrance port 58 of the sphere to a square shaped area of approximately 4 mm². The incident light reaches the sample surface at an angle of 8° to the normal direction of the sample surface. The angle of 8° is set by the sphere manufacturer since the sphere is also intended to be used for reflection measurements.

Further, the entrance port 58 is covered with a circular aperture with a diameter of 2 mm. The focus of the lens 60 is, however, not located at the entrance port, but inside the sphere 54. This means that an undisturbed light beam, i.e., when there is no sample at the entrance port 58, will diverge after passing the focus of the lens and illuminate a circular area, due to the circular aperture at the entrance port, with a diameter of approximately 7 mm at the exit port 62.

The size of the square shaped exit port 62 is 1 cm². Light passing through the entrance aperture will fall on the exit port 62 only and not on the sphere wall 64 when no sample was placed at the entrance. A light trap at the exit port 56 will absorb all light entering the sphere 54.

Spectra are obtained between 300 and 800 nm, i.e. the spectra covers the visible region between 380 and 780 nm. Total transmission spectra are acquired with a highly and diffusively reflecting Spectralon reference at the exit port 62. Diffusively scattered spectra were acquired with a light trap at the exit port 62.

Integrated values of the total and diffuse transmittance $\tau_{Total}$ and $\tau_{Diffuse}$, respectively, were calculated according to Eq. 1 below.

$$\tau(\text{Total or Diffuse}) = \frac{\int_{\lambda=380\ nm}^{700\ nm} S(\lambda)V(\lambda)\tau(\lambda)d\lambda}{\int_{\lambda=380\ nm}^{700\ nm} S(\lambda)V(\lambda)d\lambda} \quad \text{Eq. 1}$$

wherein:
$S(\lambda)$ is the relative spectral power distribution of CIE Standard Illuminant D65 as given in Table 1 in ISO/CIE 10526:1999 and is representing daylight;
$V(\lambda)$ represents the spectral luminous efficiency of a human eye as given in Table 1 in ISO/CIE 10527:1991;
$\tau(\lambda)$ is the transmission spectrum (total or diffuse transmission), and
$\lambda$ is the wavelength The total light transmittance is defined as $\tau_{Total}$.
The haze measure is calculated according to Eq. 2 below $$\text{Haze measure} = \frac{\tau_{Diffuse}}{\tau_{Total}} \quad \text{Eq. 2}$$

Where $\tau_{Total}$ and $\tau_{Diffuse}$ are defined by and calculated according to eq. 1 above. A sample is examined twice and the haze measure is calculated as the average value of the haze measures obtained from the two examinations.

A suction device according to the invention and as depicted in FIGS. 2 and 3 was made of polyurethane and its properties tested according to that method that is outlined above. The total light transmittance as well as the haze measure was measured for the attachment portion 32 as well as the inspection portion 38 of the tested suction device. The results of the measurements are presented hereinbelow:

| Tested area | $\tau_{Total}$ (%) | Haze measure (%) |
|---|---|---|
| Attachment portion | 85 | 79 |
| Inspection portion | 73 | 32 |

EXAMPLE 2

Sterilization Method

Sterilization in accordance with sterigenics cycle 38 may be used for the sterilization of a suction device. The cycle settings for a sterigenics cycle 38 are presented hereinbelow.

| Parameter | Unit | Sterigenics cycle 38 |
|---|---|---|
| Jacket temp | ° C. | 38 |
| Evacuation pressure | mbar | 255 |
| Evacuation time | hh:mm | 01:00 |
| Pre Humidification | mbar | — |
| Pre Humidification | hh:mm | — |
| Leak Rate | mbar/minutes | 15 mbar/10 min |
| Steam injection | mbar | — |
| Number of steam pulses | Number | — |
| Steam injection pressure increase during pulses | mbar | — |
| Steam dwell | hh:mm | 00:15 |
| Steam dwell pressure | mbar | 275 |
| First Nitrogen injection (final pressure) | | 345 |
| Eo Injection temperature | ° C. | >20 |
| Eo Dwell time | hh:mm | 04:00 |
| Estimated Gas concentration | mg/l | 650-750 |
| Temperature during Eo Dwell | ° C. | 40 |
| Chamber Pressure during Dwell | mbar | 790 |
| Eo Evacuation Pressure | mbar | 250 |
| Eo Evacuation Time | hh:mm | 00:19 |
| N2 or Air Washes | Number | N2/3 |
| N2 or Air Injection pressure | mbar | 900 |
| Evacuation Pressure | mbar | 250 |

Moreover, it should be noted that pre humidification is used on Sterigenics cycles, usually 12-24 hours, temperature degree of 40 Celsius and humidity >60 RH %. Additionally, aeration room is used on Sterigenics cycles, usually 96 hours, 40 degree of Celcius.

EXAMPLE 3

Surface Roughness Measurments

A suction device according to the invention and as depicted in FIGS. 2 and 3 was made of polyurethane and its properties tested according to methods outlined in Example 1. The inspection portion of this device had a haze measure of approximately 32% and total transmittance value of approximately 73%.

The surface roughness of the inspection portion of three individual suction device samples where determined using the following area surface roughness measures: $S_a$ (average deviation from average surface plane), $S_{dq}$ (average angle of surface slopes) as well as $S_{dr}$ (percentage of increased area compared to a plane). Moreover, the surface roughness of the attachment portion of one of the samples was measured. Each one of the above area surface roughness measures was determined in accordance with the following standards: ISO 25178-2:2009 and ISO 25178-3:2009.

Each one of the suction device samples was produced by a method for producing a suction device in accordance with the present disclosure, i.e. using a mould with a relatively smooth mould inspection portion 50. The surface roughness of the mould inspection portion 50 of the mould that was used for producing the suction device samples is presented hereinbelow.

Each one of the three individual samples was sterilized in accordance with the sterilization procedure outlined in Example 2 hereinabove prior to the surface roughness measurements.

In order to measure the surface roughness, a Bruker NPFlex optical profiler, using 10× magnification and VSI (vertical scanning inferometry) mode was used. For each one of the three individual samples, an area of the outer surface 38" was analysed. The measured area was 620×470 µm. Each sample is examined twice and the below surface roughness measures are calculated as the average value of the surface roughness measures obtained from the two measurements.

| Sample # | $S_a$ (nm) | $S_{dq}$ (°) | $S_{dr}$ (%) |
|---|---|---|---|
| Inspection portion 1 | 1320 | 17.1 | 3.7 |
| Inspection portion 2 | 1213 | 18.9 | 5.0 |
| Inspection portion 3 | 1485 | 14.4 | 3.1 |
| Attachment portion | 1686 | 20.5 | 5.8 |

Moreover, the surface roughness was measured for a mould 48 with a mould inspection portion 50 as illustrated in FIG. 4. The mould inspection portion 50 was polished using a diamond paste with particles the size of which are 1 micron.

The following surface roughness measurements were obtained for the mould inspection portion 50.

| Item | $S_a$ (nm) | $S_{dq}$ (°) | $S_{dr}$ (%) |
|---|---|---|---|
| Mould inspection portion | 1432 | 15.0 | 3.4 |

EXAMPLE 4

Structural Strength of a Suction Device

A suction device according to the invention and as depicted in FIGS. 2 and 3 was made of polyurethane and its properties tested according to methods outlined in Examples 1 and 3. This device had a haze measure of approximately 32%, total transmittance value of approximately 73%, and surface roughness of $S_{dq}$ 17° at the outer surface 38" of the inspection portion 38. The thickness of the device in the inspection portion 38 was between 0.7 mm and 0.9 mm. As shown in FIG. 3, the device comprised a partition wall 42 underneath the inspection portion 38. Thus, the inspection portion 38 was separated by the partition wall 42 and the surface area of one of the inspection sub portions was approximately 40 mm² and the surface are of the other inspection sub portion was approximately 32 mm².

The device was adhered to a flat surface by an adhesive and was connected to a negative pressure source via the device's fluid outlet. In this example, a pump was used as the negative pressure source. Negative pressure was applied at −200 mm Hg for 2 hours. No collapse or indentation of the device at the inspection portion was observed during the time in which negative pressure was applied. Thus, the integrity of the device was maintained under negative pressure.

The invention claimed is:

1. A suction device comprising an attachment portion adapted to be attached to a wound cover member, said suction device comprising a fluid inlet being at least partially circumscribed by said attachment portion, said suction device also comprising a fluid outlet, said suction device further comprising a connection portion adapted to, at least during one operation condition of said suction device, provide a fluid communication between said fluid inlet and said fluid outlet, wherein said connection portion comprises a duct wall at least partially defining a connection duct from said inlet to said outlet, said connection portion comprising a partition wall extending at least partially from said duct wall, wherein said fluid inlet extends in a circumferential direction, said fluid inlet further extending in an axial direction being substantially perpendicular to said circumferential direction, wherein said partition wall does not extend in the circumferential direction.

2. The suction device according to claim 1, wherein said fluid outlet extends in a longitudinal direction (L), said partition wall extending in a partition wall extension ($E_{PW}$) that is substantially parallel to said longitudinal direction (L).

3. The suction device according to claim 1, wherein a projection of at least a portion of said partition wall, in said axial direction and towards said inlet, is located within said inlet.

4. A kit for a negative pressure wound therapy system, said kit comprising:
   a suction device according to claim 1;
   a wound cover member adapted to be attached over a wound.

5. The kit according to claim 4, wherein said wound cover member comprises a wound cover film.

6. The kit according to claim 4, wherein said kit further comprises fluid communication means adapted to provide a fluid communication between said fluid outlet and a negative pressure source.

7. A method comprising:
   providing a cover member,
   providing the suction device according to claim 1,
   providing said cover member with an opening,
   positioning said suction device such that said fluid inlet aligns with said opening in said cover member.

8. The method according to claim 7, further comprising:
   applying suction to said suction device.

9. A fluid communication assembly comprising the suction device according to claim 1,
   i) wherein the fluid outlet comprises a first channel that is in fluid communication with a first conduit configured to provide a fluid communication with a negative pressure source; and
   ii) wherein the fluid outlet further comprises a second channel that is in fluid communication with a second conduit configured to provide a fluid communication to a source of air for introducing an air volume into the suction device.

10. The fluid communication assembly according to claim 9, wherein the fluid communication assembly further comprises the negative pressure source, wherein the first conduit is in fluid communication with the negative pressure source.

11. The fluid communication assembly according to claim 9, wherein the source of air is ambient air.

12. The fluid communication assembly according to claim 9, wherein the first channel and the second channel enters the connection portion on a respective side of the partition wall.

\* \* \* \* \*